(12) United States Patent
Arber et al.

(10) Patent No.: US 10,772,590 B2
(45) Date of Patent: Sep. 15, 2020

(54) AIR TRANSPORTATION SYSTEM

(71) Applicant: Elekta Limited, West Sussex (GB)

(72) Inventors: Philip Lee Arber, Horsham (GB); Clifford William Perkins, Crawley (GB); Leila Baha, Middlesex (GB)

(73) Assignee: Elekta Limited, West Sussex (GB)

( * ) Notice: Subject to any disclaimer, the term of this patent is extended or adjusted under 35 U.S.C. 154(b) by 49 days.

(21) Appl. No.: 16/150,663

(22) Filed: Oct. 3, 2018

(65) Prior Publication Data

US 2019/0105005 A1  Apr. 11, 2019

(30) Foreign Application Priority Data

Oct. 5, 2017 (GB) .................................. 1716297.5

(51) Int. Cl.
| | |
|---|---|
| *A61B 6/00* | (2006.01) |
| *A61N 5/10* | (2006.01) |
| *G01R 33/48* | (2006.01) |
| *A61B 6/03* | (2006.01) |
| *G01R 33/38* | (2006.01) |
| *A61N 5/00* | (2006.01) |
| *H05G 1/02* | (2006.01) |

(52) U.S. Cl.
CPC ............ *A61B 6/4488* (2013.01); *A61B 6/035* (2013.01); *A61B 6/4435* (2013.01); *A61N 5/1049* (2013.01); *A61N 5/1081* (2013.01); *G01R 33/4808* (2013.01); *A61N 2005/005* (2013.01); *G01R 33/3804* (2013.01); *H05G 1/025* (2013.01)

(58) Field of Classification Search
CPC ..... A61B 6/035; A61B 6/4435; A61B 6/4488; A61N 5/103; A61N 5/1049; A61N 5/1081; A61N 2005/005; G01R 33/3804; G01R 33/4808; H05G 1/025
See application file for complete search history.

(56) References Cited

U.S. PATENT DOCUMENTS

| | | | |
|---|---|---|---|
| 5,299,249 | A | 3/1994 | Burke et al. |
| 2004/0202287 | A1 | 10/2004 | Müller |
| 2004/0228450 | A1 | 11/2004 | Mueller |

(Continued)

FOREIGN PATENT DOCUMENTS

| | | |
|---|---|---|
| DE | 102011081257 A1 | 2/2013 |
| EP | 2343103 A1 | 7/2011 |

(Continued)

OTHER PUBLICATIONS

"European Application Serial No. 18 198 449.3, Extended European Search Report dated Feb. 14, 2019", (Feb. 14, 2019), 6 pgs.

(Continued)

*Primary Examiner* — Mark R Gaworecki
(74) *Attorney, Agent, or Firm* — Schwegman Lundberg & Woessner, P.A.

(57) ABSTRACT

Described is an image guided radiation therapy (IGRT) apparatus comprising a medical imaging device and a radiation source, wherein the radiation source is provided on a gantry which surrounds the medical imaging device. The apparatus further comprises ducting for directing cool air from a source of cool air to a gap between the gantry and the medical imaging device.

40 Claims, 8 Drawing Sheets

(56) References Cited

U.S. PATENT DOCUMENTS

| | | | |
|---|---|---|---|
| 2005/0135560 A1* | 6/2005 | Dafni | A61B 6/4405 378/101 |
| 2006/0126782 A1* | 6/2006 | Pohan | G01T 1/1648 378/19 |
| 2006/0215808 A1 | 9/2006 | Lacey | |
| 2006/0285639 A1* | 12/2006 | Olivera | A61N 5/1042 378/65 |
| 2009/0041181 A1 | 2/2009 | Krug | |
| 2015/0270092 A1 | 9/2015 | Gruchatka et al. | |
| 2017/0105692 A1 | 4/2017 | Sawanobori | |
| 2018/0059270 A1* | 3/2018 | Hefetz | G01T 1/244 |

FOREIGN PATENT DOCUMENTS

| | | |
|---|---|---|
| WO | WO-2011008969 A1 | 1/2011 |
| WO | WO-2015197475 A1 | 12/2015 |

OTHER PUBLICATIONS

"United Kingdom Application Serial No. 1716297.5, Search Report dated Nov. 2, 2017", (dated Nov. 2, 2017), 4 pgs.

* cited by examiner

AIR TRANSPORTATION SYSTEM

CLAIM OF PRIORITY

This application claims the benefit of priority of United Kingdom Application No. GB 1716297.5, filed Oct. 5, 2017, which is hereby incorporated by reference in its entirety.

TECHNICAL FIELD

The present disclosure relates to an image guided radiation therapy (IGRT) apparatus. More particularly the present disclosure provides an IGRT apparatus comprising a cooling system.

BACKGROUND

Radiation therapy is a localised treatment designed to treat an identified tissue target (such as a cancerous tumour) and spare the surrounding normal tissue from receiving doses above specified tolerances thereby minimising risk of damage to healthy tissue. Prior to delivery of radiation therapy, an imaging system can be used to provide a three-dimensional image of the target from which the target's size and mass can be estimated and an appropriate treatment plan determined.

Many factors may contribute to differences between the dose distribution determined in the treatment plan and the delivered dose distribution. One such factor is an inconsistency between the patient position at the imaging stage and the patient position in the radiation treatment unit.

Image guided radiation therapy (IGRT) involves the use of an imaging system to view target tissues whilst radiation treatment is being delivered to the target tissue. IGRT incorporates imaging coordinates from the treatment plan to ensure the patient is properly aligned for treatment in the radiation therapy device.

Various medical imaging technologies are used to identify target tissues in radiation therapy planning and IGRT. These include (without limitation); Computed Tomography (CT), Positron Emission Tomography (PET), ultrasound imaging and Magnetic Resonance Imaging (MRI).

The Applicant's prior published international patent application no. WO03/008986 describes a device for use in IGRT which includes the functions of an MRI device in a radiation therapy treatment apparatus and proposes technology for overcoming the problems in doing so. The device comprises a large ring gantry onto which a linear accelerator is mounted and arranged to travel around a target positioned at the isocentre of the ring. An MRI sits in the aperture of the ring gantry sharing the isocentre. A body to be treated is introduced into a treatment space at the isocentre by means of a sliding table.

SUMMARY

The use of various devices within dose proximity to one another means that the apparatus can suffer from overheating problems. These problems are often solved by the use of complex and sizeable cooling systems, which require large spaces in which to operate. Further problems are also associated with the use of cooling systems in relation to the cooling of a rotating gantry and devices mounted thereon. For example, certain water cooling systems include a reeling system of water pipes that are required to not continuously rotate. There are significant restrictions placed on an IGRT cooling system because the IGRT system is large and housed within a confined space. The present subject matter seeks to alleviate the problems associated with cooling systems for IGRT apparatus.

According to one aspect of the present disclosure, there is provided an image guided radiation therapy (IGRT) apparatus comprising a medical imaging device and a radiation source, wherein the radiation source is provided on a gantry which surrounds the medical imaging device, the apparatus further comprising ducting for directing cool air from a source of cool air to a gap between the gantry and the medical imaging device.

In the context of the present disclosure, it is to be understood that "ducting" refers to a passageway or elongate cavity that carries and directs cool air. It is to be understood that the passageway can be enclosed with openings at each of its ends or can be an open structure shaped to direct cool air.

Preferably, the gantry is rotatable about the medical imaging device. More preferably, the gantry is freely rotatable about the medical imaging device.

Preferably, the ducting comprises an annular duct for directing cold air into the gap between the gantry and the medical imaging device.

More preferably, the ducting for directing cool air from a source of cool air to a gap between the gantry and the medical imaging device comprises at least one flexible hose and an annular duct.

Preferably, the annular duct is provided between the gantry and the medical imaging device turret.

Preferably, the annular duct is positioned around the medical imaging device.

Preferably, the gantry is rotatable about the annular duct.

Preferably, the annular duct comprises an inlet for receiving cool air, preferably wherein the inlet is positioned at, or near, the base of the annular duct.

It is understood that the "base of the annular duct" refers to the base, i.e. the floor of the treatment room in which the annular duct and the IGRT are housed. This means that cool air enters the annular duct at a position where it can rise, thus aiding movement of air towards the top of the IGRT. This is also advantageous because it means that the lower part of the IGRT, which would likely be positioned within a hole or pit in the treatment room floor, is closest to the entry of cool air into the gantry. Since this lower part of the IGRT is often difficult to cool, such an arrangement aides cooling considerably.

Preferably, the annular duct comprises a plurality of segments. This allows the annular duct to be installed around the medical imaging device.

Preferably, the annular duct comprise at least one segment have a substantially L-shaped, curved profile. Optionally, the annular duct comprise at least one segment have a substantially U-shaped, curved profile.

Preferably, one of the segments is an inlet segment and comprises an inlet for receiving air from a first section of the ducting into the annular duct.

Preferably, the annular duct comprises an annular outlet for releasing air into the gap between the gantry and the medical imaging device.

Preferably, the annular duct is shaped to fit around the medical imaging device.

Preferably, the gantry comprises one or more air directing members for directing air from the ducting in a direction towards the outside of the gantry.

Preferably, the gantry comprises one or more air directing members for directing air away from a position below the gantry. This is particularly advantageous because it is common for a gantry to sit within a hole in the floor and so, if warmed air is allowed to sit within the hole, i.e. beneath the gantry, this can hinder cooling of the gantry.

Preferably, the air directing members are configured for directing air towards the outside of the gantry as the gantry rotates about the medical imaging device.

Preferably, the air directing members are configured for directing air towards the outside of the gantry as the gantry rotates about the annular duct.

Preferably, the one or more air directing members comprise one or more baffle plates.

Preferably, the gantry comprises one or more fans for directing air from the ducting to the outside of the gantry.

Preferably, the gantry comprises a water conditioning system for cooling the components on the gantry.

Preferably, the water conditioning system is a water cooling system. Further preferably, the water conditioning system is a water cooling and water heating system.

Preferably, the water conditioning system comprises one or more heat exchangers.

Preferably, the gantry comprises one or more air directing members for directing air past the one or more heat exchangers.

Preferably, the gantry comprises one or more air directing members for preventing or reducing the amount of warmed air re-circulating past the one or more heat exchangers.

Preferably, the one or more air directing members comprise one or more fans and/or one or more baffle plates.

Preferably, the gantry comprises one or more plenums.

Within this specification, it will be appreciated that a "plenum" is an enclosed chamber within the gantry or water conditioning system into which air circulating through the gantry is unable to pass.

Preferably, the gantry comprises one or more plenums for separating the one or more heat exchangers from re-circulating warmed air.

In this respect, in embodiments comprising one or more plenums, the plenums provide an enclosed space into which warmed air cannot pass. In addition, by reducing the available air flow passages within the gantry, re-circulation of warmed air back into the gantry is significantly reduced because the available air flow passages in the gantry are filled with air moving radially outward from the ducting and across the gantry.

Preferably, the gantry comprises one or more plenums positioned radially inward of the one or more heat exchangers.

Preferably, each heat exchanger comprises or is positioned adjacent one or more plenums.

Preferably, the gantry comprises a plurality of apertures through which air can pass.

Preferably, the gantry comprises an inlet for the passage of air from the gap between the gantry and the medical imaging device. Preferably, the inlet is oval-shaped or rectangular-shaped, having rounded ends.

Preferably, the apparatus comprised flexible ducting for connecting the annular duct to a source of cool air. This is advantageous because it allows the air conditioning unit to be positioned in a variety of locations best suited to the available electrical and/or water connections of a room. For example, this is particularly advantageous in embodiments wherein the air conditioning unit is to be connected to the cold water supply of a building.

Preferably, the source of cool air is a heat exchanger; for example, an air conditioning unit.

As such, in some embodiments, the apparatus further comprises a source of cool air, such as an heat exchanger; for example, an air conditioning unit.

Preferably, the heat exchanger is a portable heat exchanger.

Preferably, the heat exchanger comprises an inlet for receiving warm air, one or more heat exchangers for cooling the received warm air and an outlet for expelling cooled air. Preferably, the outlet is for connection to the ducting.

Preferably, the heat exchanger is connectable to a cold water system; for example, a cold water system of a building; preferably a hospital. In this way, the heat exchangers can be provided with a particularly convenient supply of cold water for cooling the warm air entering the inlet.

Preferably, the air conditioning unit comprises a condensate pump.

Preferably, the air conditioning unit comprises a drain for connection to the drainage system of a building; for example, a hospital.

Preferably, the gantry comprises a static ring component and a dynamic ring component upon which a radiation source is mounted, the dynamic ring component being rotatable about the ring centre.

According to another aspect of the present disclosure, there is provided a gantry for surrounding a medical imaging device, the gantry comprising ducting for directing cool air from a source of cool air to a gap between the gantry and a medical imaging device.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein and vice versa.

It will be appreciated that reference to "one or more" includes reference to "a plurality".

BRIEF DESCRIPTION OF THE DRAWINGS

An embodiment of the disclosure will now be described with reference to the accompanying Figures in which.

DETAILED DESCRIPTION

Figure 1A:
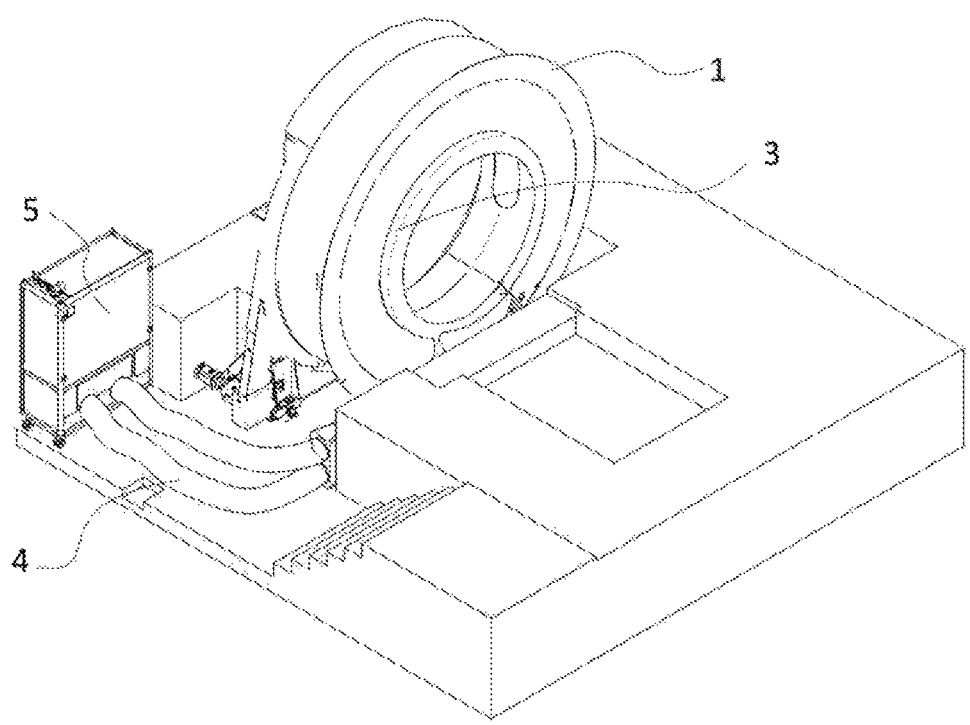
FIGS. 1A and 1B show a perspective view of an image guided radiation therapy (IGRT) apparatus in accordance with the present disclosure.
Figure 1B:
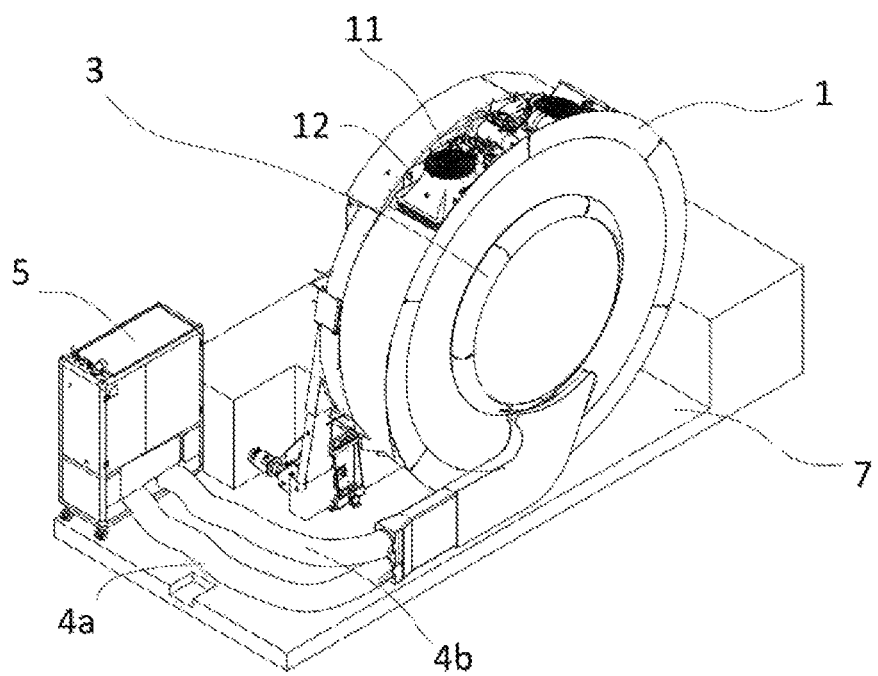

FIGS. 1A and 1B show an image guided radiation therapy (IGRT) apparatus in accordance with the present disclosure. In use, the radiation therapy apparatus comprises a linear accelerator (LINAC) mounted on the gantry 1 and an MRI scanner (not shown) sits in the aperture of the ring gantry 1 sharing the isocentre. A body to be treated is introduced into a treatment space at the isocentre by means of a sliding table (not shown). The gantry 1 is typically of the order of 2-3 metres in diameter. The IGRT apparatus further comprises a beam emitting module and a beam shaping module (not shown), which are transported around the target by means of the gantry 1.

Ducting 3, 4 is proved for directing cool air from a heat exchanger 5 to a gap (not shown) between the gantry 1 and the medical imaging device.

The ducting includes an annular duct 3 positioned around the medical imaging device for pushing cold air into the gap between the gantry 1 and the medical imaging device and a pair of flexible ducts/hoses 4a, 4b for connecting the annular duct 3 to the portable heat exchanger 5. The gantry 1 is rotatable about the annular duct 3. The annular duct 3 is also connected to the cryostat 3 of the MRI device; the concrete pit 7 in the floor of the treatment room and the RF cage (not shown).

The annular duct 3 is shown in greater detail with reference to FIG. 1B and FIGS. 5A to 5C. The annular duct 3 is vacuum-formed out of ABS (acrylonitrile butadiene styrene) and has a thickness of around 4 mm.

Figure 5A:
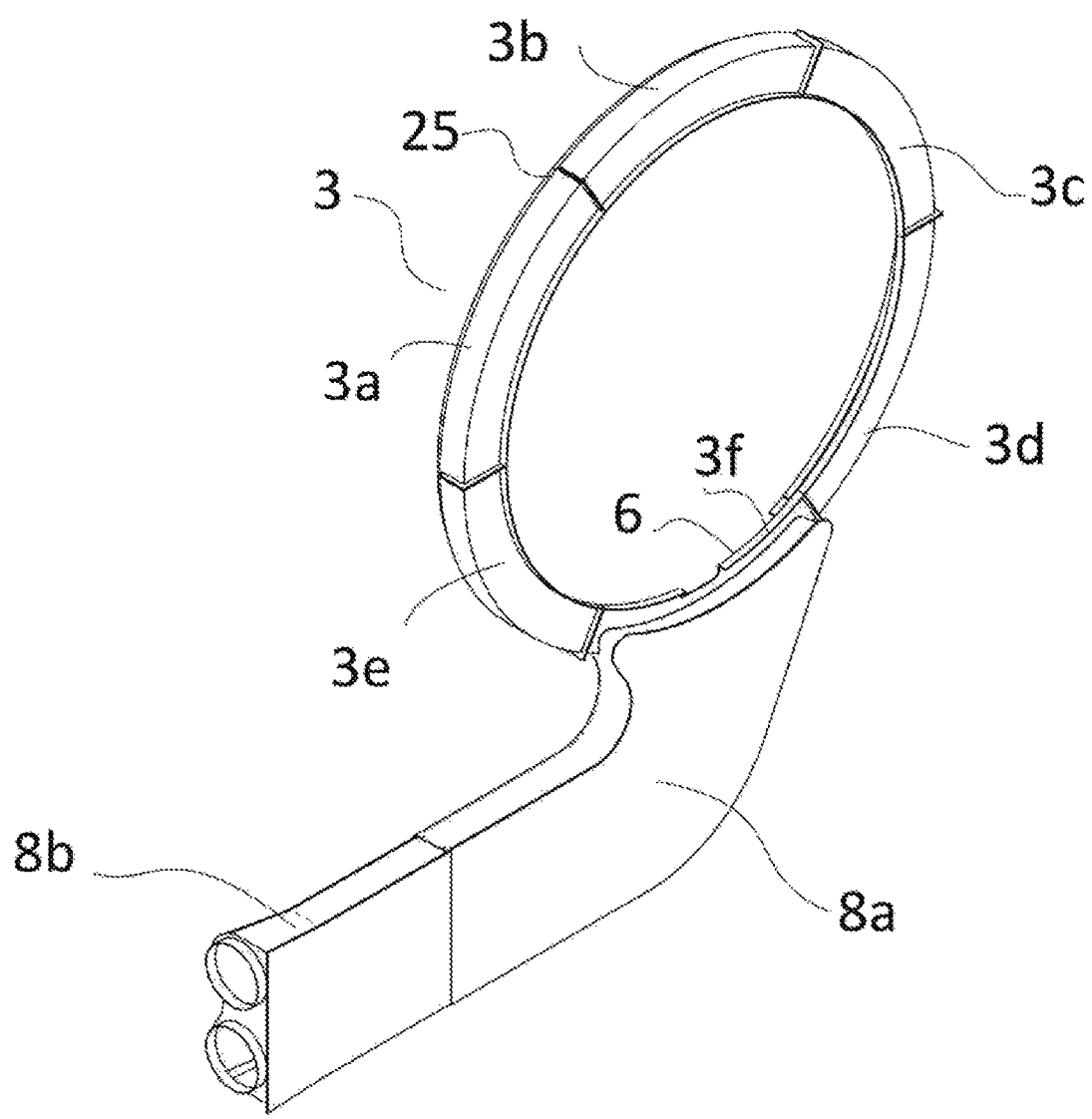
FIG. 5A shows the components of an annular duct of the IGRT apparatus.

Referring to FIG. 5A, the annular duct 3 comprises an inlet 6 for receiving cool air in to an air inlet segment 3f of the annular duct 3. The inlet 6 is positioned at the base of the annular duct 3. This means that cool air enters the annular duct 3 at a position where it can rise, thus aiding general movement of air towards the top of the IGRT device. Referring to FIG. 1B, this is also advantageous because it means that the lower part of the IGRT, which is positioned within a pit 7 in the treatment room floor, is closest to the entry of cool air into the gantry 1. The annular duct 3 includes an annular outlet 25, in the form of an open face of the annular duct, for releasing air into the gap between the gantry 1 and the medical imaging device.

Figure 5B:
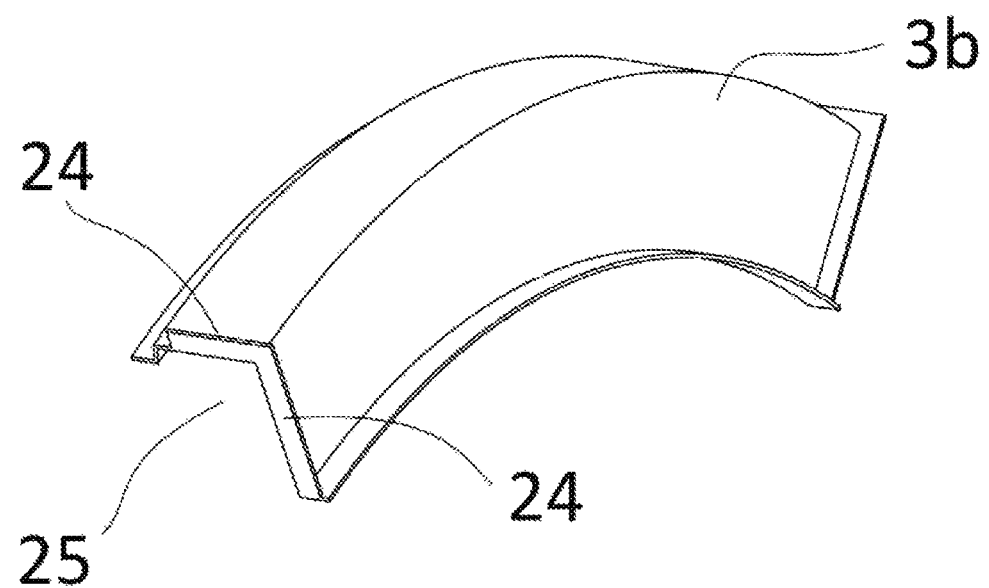
FIG. 5B shows an annular duct main segment and 5C shows an annular duct air inlet segment for use in the IGRT apparatus.
Figure 5C:
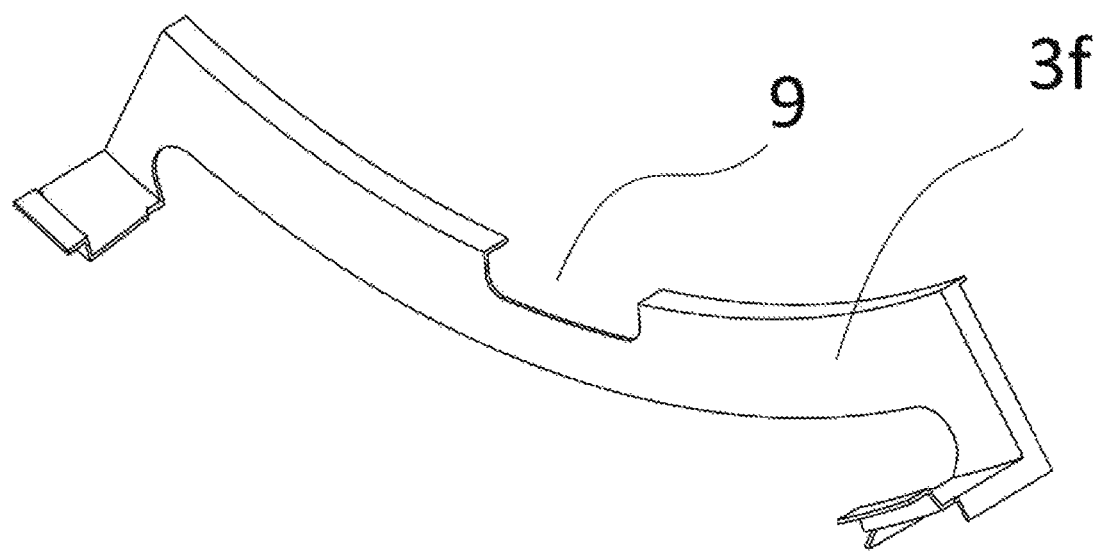

Referring to FIGS. 5A and 5B, the annular duct 3 comprises a plurality of segments 3a, 3b, 3c, 3d, 3e, 3f. This allows the annular duct to be installed after the medical imaging device (not shown). As will be apparent from FIG. 5A, one of the segments 3f comprises the inlet 6. Two tabs 24 are provided on opposing ends of each segment 3a, 3b, 3c, 3d, 3e, 3f to attach the segments together. In the example shown, each tab 24 has have an outward angle of 3 degrees. This enables the tabs to be pushed against each other and create a seal. As shown in FIG. 5B, the profile of the segment 3b of the annular duct 3 is substantially L-shaped with an upstanding U-shaped lip protruding from one wall of the segment 3b.

The inlet segment 3f is connected to joining piece 8a which, together with joining piece 8b provides a rigid support connecting the annular duct 3 with the flexible hoses 4a, 4b. In a preferred embodiments, the flexible ducts 4 are each 250 mm diameter and have a quick-release connection to the joining piece 8b. The joining piece 8b allows for a dedicated cold air supply from the portable heat exchanged 5 to the annular duct 3. In the example shown in FIG. 5C, the annular duct segment 3f includes a notch 9, which is shaped to fit around the cryostat of the medical imaging device.

Figure 4:
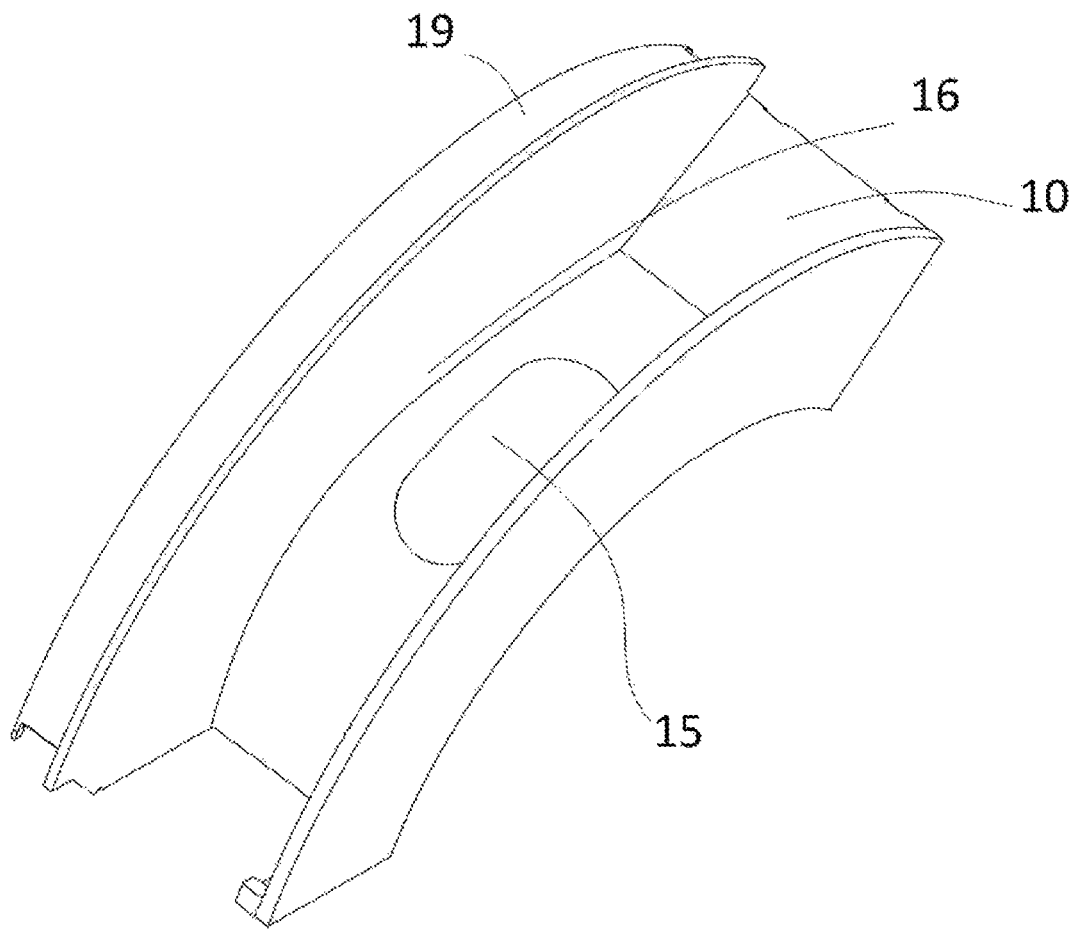
FIG. 4 shows a gantry segment for receiving a water conditioning unit.

Referring to FIG. 4, each gantry segment 1a of the IGRT apparatus comprises a plurality of baffle plates 10 for directing air from the annular ducting 3 in a direction radially outward towards the outside of the gantry 1; for example, as the gantry 1 rotates, in use. Fans 11 are also provided for directing air and, in the embodiment shown, also form part of a water conditioning system 12 for cooling the gantry 1. The water conditioning system 12 is connected to a water distribution unit (not shown), which distributes the water around the gantry 1 to cool the gantry 1 and components mounted thereon. The water conditioning system 12 provides water cooling of the components of the beam generation module (not shown). The water conditioning system 12 is a self-contained, temperature controlled water cooling and heating system, which is designed to provide water that is regulated to 30±5° C. The water conditioning system 12 is able to cool water in the system during operation and also heat water in the system before operation so that the apparatus can be provided at the required operating temperature for start-up.

Figure 2:
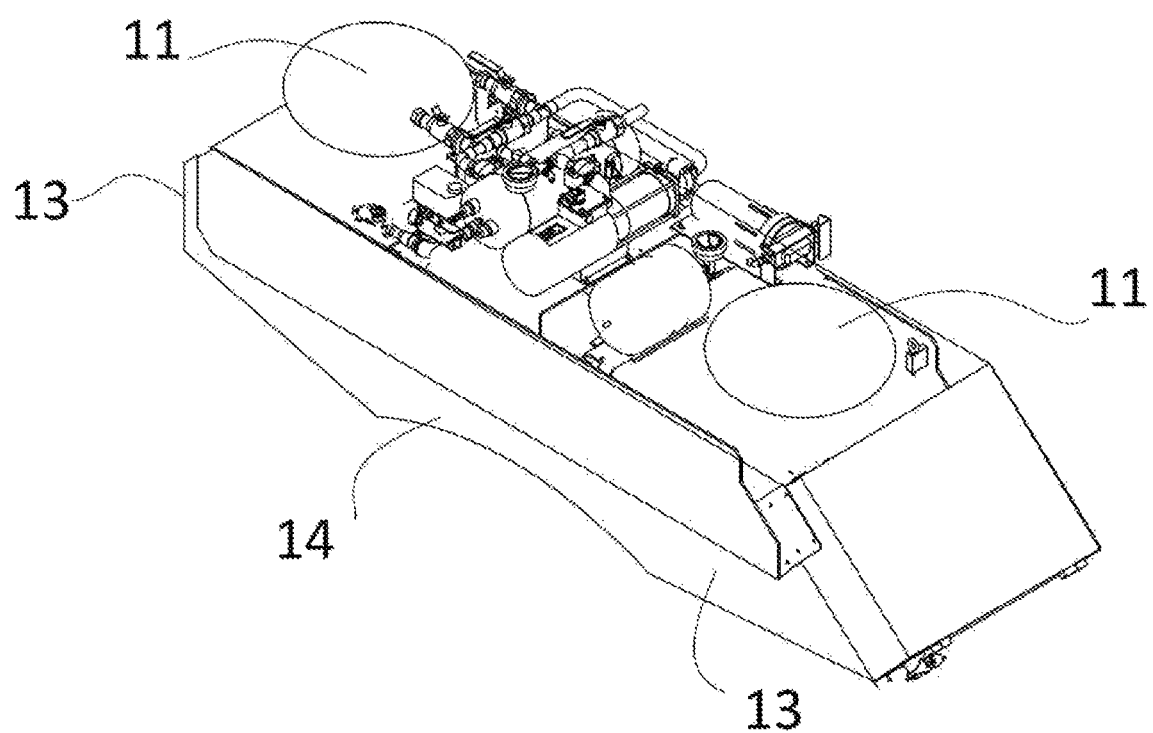
FIG. 2 shows a water conditioning system for use in the IGRT apparatus.

With reference to FIG. 2, a water conditioning system 12 includes a pair of fans 11 which draw air past a pair of heat exchangers 13. A plenum/chamber 14 is provided and positioned radially inward of the water conditioning system 12. The plenums 14 provide an enclosed space into which warmed air cannot pass. Thus, re-circulation of warmed air back into the gantry 1 is significantly reduced because the available air flow passages of the gantry 1 are filled with air moving radially outward from the ducting 3 and across the gantry 1.

The gantry 1 includes a plurality of gantry segments 1a. A water conditioning system 12 resides in each gantry segment 1a. Each gantry segment 1a includes apertures 15 through which air can pass. With reference to FIG. 4, one such aperture 15 forms an inlet for cool air to pass from the space between the gantry 1 and the medical imaging device. The aperture 15 comprises a cut-out in the gantry segment 1a, which is oval-shaped. In alternative embodiments, the aperture 15 comprises two circular apertures, or a rectangular aperture having rounded ends. The aperture 15 ensures that the water conditioning system 12 has the required dedicated flow of cold air, but does not jeopardise the structural integrity of the gantry 1. The gantry 1 is also provided with mounts 16 to which the water conditioning system 12 can be attached. As will be appreciated, the annular duct 3 provides cooling for electronics on the gantry 1 and the expelled cold air also cools down the room to some extent.

Figure 3A:
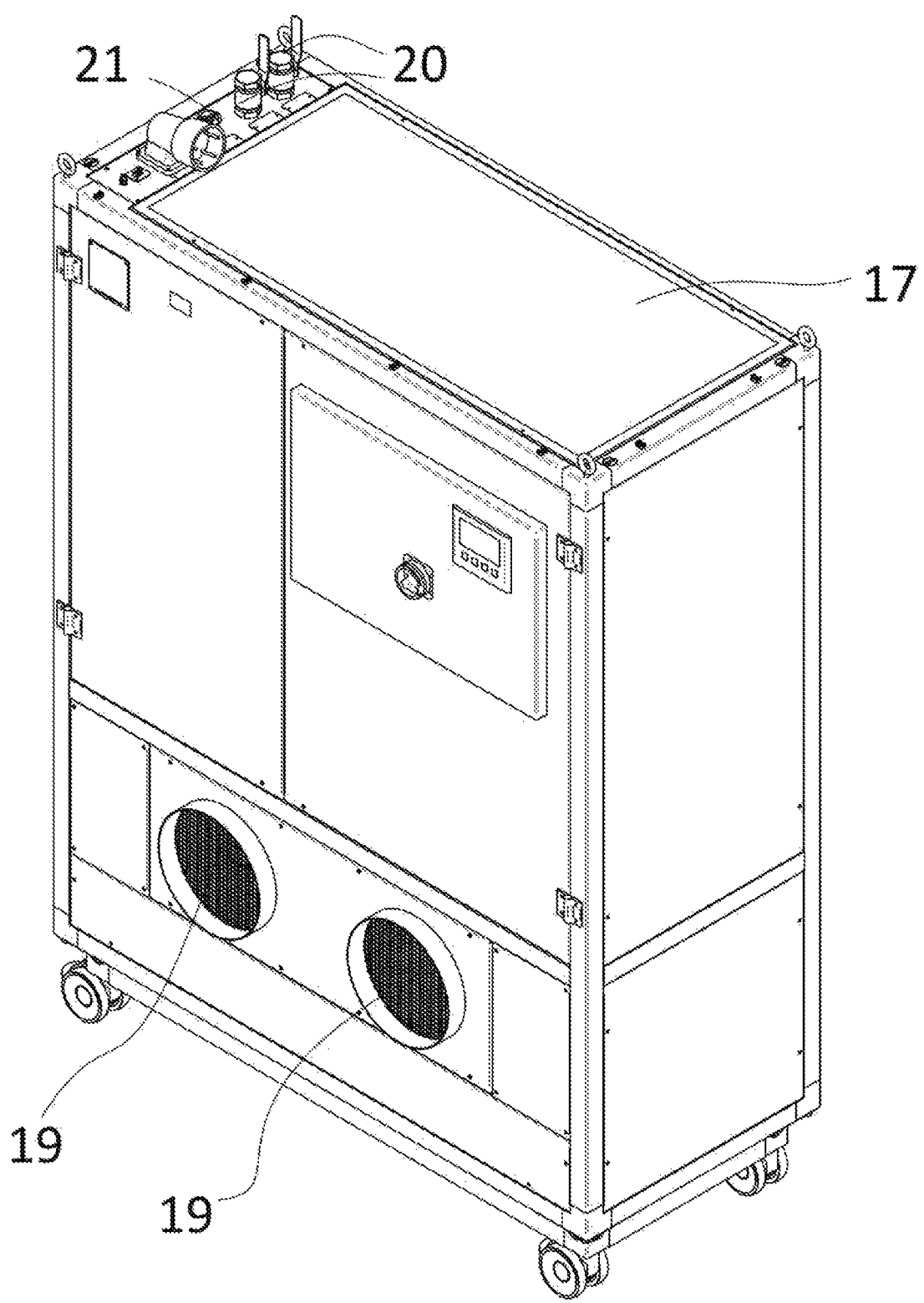
FIGS. 3A and 3B shows the components and a view of the inside of a heat exchanger for use in the IGRT apparatus.
Figure 3B:
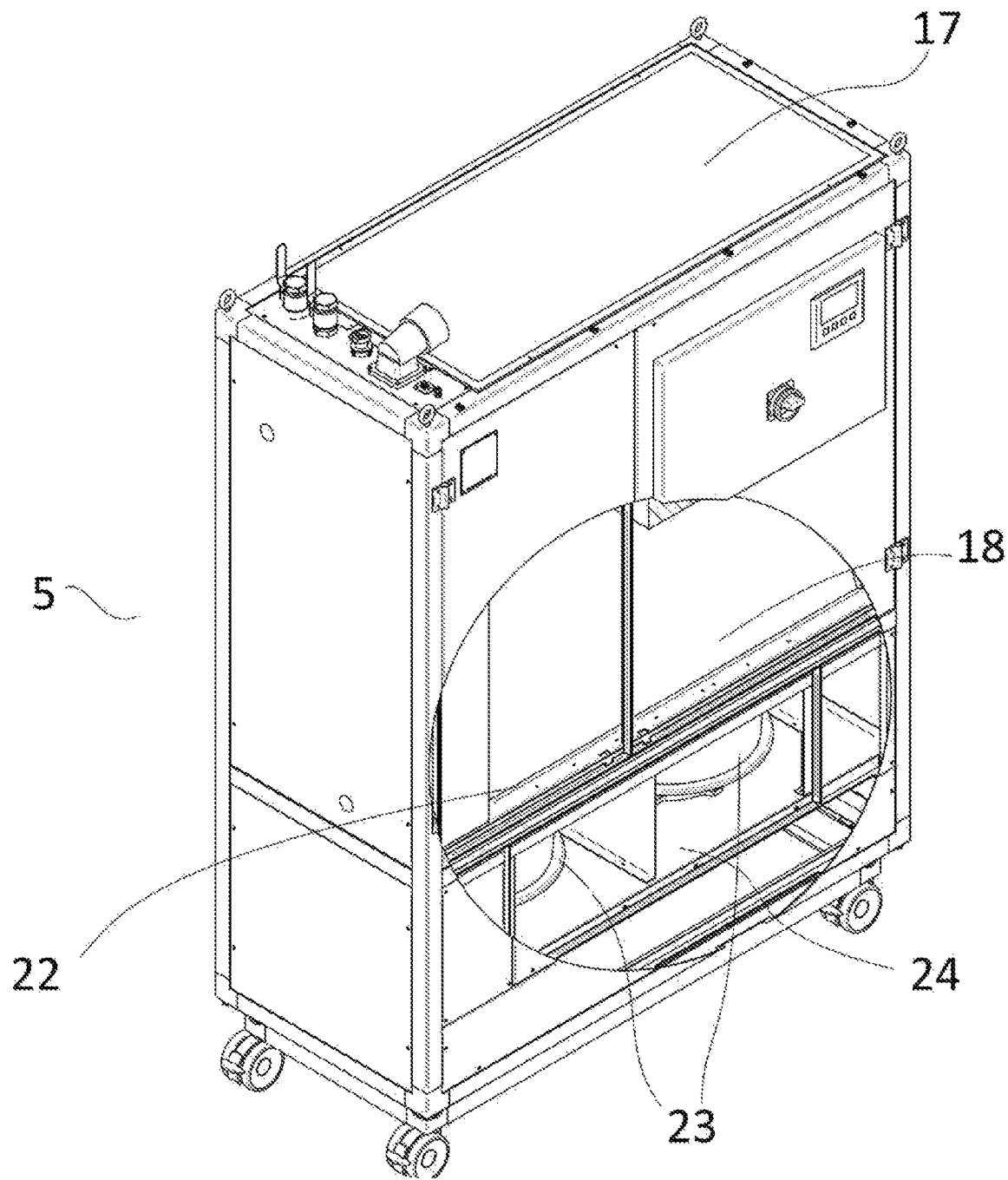

With reference to FIG. 3A and FIG. 3B, a portable heat exchanger 5 is shown in more detail. The portable heat exchanger 5 is connected to the annular duct 3 by flexible ducts 4a, 4b. The portable heat exchanger includes an air inlet grille 17 for receiving warm air, a heat exchanger 18 for cooling the received warm air, and outlets 19 for expelling cooled air. The outlets 19 are for connection to the flexible ducts/hoses 4a, 4b, shown in FIG. 1B.

The portable heat exchanger 5 is connectable to a cold water system; for example, a cold water system of a building, via water flow/return connectors 20. A condensate pump (not shown) is provided together with a condensate pipe connector 21 for connection to the drainage system of a building; for example, a hospital. The portable heat exchanger 5 can be connected to a hospital chiller in order to provide chilled water for the heat exchanger 18. Also shown in FIGS. 3A and 3B are a condensate drip tray 22, centrifugal fans 23 and air outlet connection plenums 24.

The portable heat exchanger 5 provides cold air for the water conditioning system 12 to ensure that the temperature difference between the water inside the water conditioning system 12 and the air around the heat exchangers 13 is large enough to provide efficient cooling.

In use, the portable heat exchanger 5 pulls in warm air through the air inlet grill 17 at the top of the unit. It cools the air to 14±2° C. and blows the air out into the interface of the unit with the flexible ducts 4a, 4b. The flexible ducts 4a, 4b carry the cold air to the interface with the annular duct 3. The annular duct 3 in turn transfers this cold air in through the air inlet 6, around the annular duct 3. The annular duct 3 in the gap between the medical imaging device and the gantry 1 provides dedicated cold air to the inlet of the water conditioning system and ensures that the temperature difference between the water in the water conditioning system 12 and the air that surrounds the heat exchangers is maintained as required. The cold air reaches the plenum 14 on the water conditioning system 12 through the aperture 15 in the gantry segment 1a, where the water conditioning system 12 resides. The air then gets pulled through the heat exchangers 13 by the fans 11 and it cools the water inside the heat-exchangers 13 of the water conditioning system 12. The warmer air gets blown away from the circumference of the water conditioning system 12 and gantry 1 by the fans 11. The warm air will mix again with the air inside of the treatment room and reach the portable heat exchanger 5, passing into the inlet grill of the portable heat exchanger 5 as the cycle continues.

With reference to FIG. 2, the plenum 14 of the water conditioning system 12 isolates the heat exchangers 13 from their surroundings. It ensures that the cold air is directed right through to the heat exchangers 13 and also that no warm air from the fans 11 is re-circulated back near the heat exchangers 13. This improvement was found to ensure that the water conditioning system 12 maintains the desired temperature of around 30±5° C. regardless of the gantry position; i.e. the angle of rotation of the gantry 1. It was found that re-circulation of the hot air is prevented, so that the efficiency and cooling capacity of the heat exchangers 13 is maintained.

Further embodiments and variations of the embodiments disclosed herein will no doubt occur to the skilled addressee without departing from the true scope of the claims of the invention as defined in the appended claims, which are hereby incorporated by reference in the present Detailed Description, including all permutations and combinations thereof, or of features or aspects thereof, except those explicitly indicated in the present Detailed Description as being mutually exclusive of each other.

The invention claimed is:

1. An image guided radiation therapy (IGRT) apparatus comprising a medical imaging device and a therapeutic radiation source, wherein the radiation source is provided on a ring gantry about the medical imaging device, wherein the medical imaging device comprises an MRI scanner in an aperture of the ring gantry; the apparatus further comprising an annular duct for directing cool air from a source of cool air to a gap between the gantry and the medical imaging device.

2. An IGRT apparatus according to claim 1 wherein the gantry is rotatable about the medical imaging device.

3. An IGRT apparatus according to claim 1 wherein the gantry is freely rotatable about the medical imaging device.

4. An IGRT apparatus according to claim 1 wherein the annular duct for directing cool air from a source of cool air to a gap between the gantry and the medical imaging device comprises at least one flexible hose and an annular duct.

5. An IGRT apparatus according to claim 4 wherein the annular duct is provided between the gantry and a turret of the medical imaging device.

6. An IGRT apparatus according to claim 4 wherein the annular duct is positioned around the medical imaging device.

7. An IGRT apparatus according to claim 4 wherein the gantry is rotatable about the annular duct.

8. An IGRT apparatus according to claim 4 wherein the annular duct comprises an inlet for receiving cool air.

9. An IGRT apparatus according to claim 8 wherein the inlet is positioned at, or near, a base of the annular duct.

10. An IGRT apparatus according to claim 4 wherein the annular duct comprises a plurality of segments.

11. An IGRT apparatus according to claim 10 wherein the annular duct comprises at least one segment having a substantially L-shaped, curved profile.

12. An IGRT apparatus according to claim 10 wherein the annular duct comprises at least one segment have a substantially U-shaped, curved profile.

13. An IGRT apparatus according to claim 10 wherein one of the segments is an inlet segment and comprises an inlet for receiving air from a first section of the ducting into the annular duct.

14. An IGRT apparatus according to claim 4 wherein the annular duct comprises an annular outlet for releasing air into the gap between the gantry and the medical imaging device.

15. An IGRT apparatus according to claim 4 wherein the annular duct is shaped to fit around the medical imaging device.

16. An IGRT apparatus according to claim 1 wherein the gantry comprises one or more air directing members for directing air from the ducting in a direction towards the outside of the gantry.

17. An IGRT apparatus according to claim 16 wherein the one or more air directing members comprise one or more baffle plates.

18. An IGRT apparatus according to claim 1 wherein the gantry comprises one or more air directing members for directing air away from a position below the gantry.

19. An IGRT apparatus according claim 18 wherein the air directing members are configured for directing air towards the outside of the gantry as the gantry rotates about the medical imaging device.

20. An IGRT apparatus according to claim 18 wherein the air directing members are configured for directing air towards the outside of the gantry as the gantry rotates about the annular duct.

21. An IGRT apparatus according to claim 1 wherein the gantry comprises one or more fans for directing air from the ducting to the outside of the gantry.

22. An IGRT apparatus according to claim 1 wherein the gantry comprises a water conditioning system for cooling one or more components on the gantry.

23. An IGRT apparatus according to claim 22 wherein the water conditioning system is a water cooling system.

24. An IGRT apparatus according to claim 22 wherein the water conditioning system is a water cooling and a water heating system.

25. An IGRT apparatus according to claim 22 wherein the water conditioning system comprises one or more heat exchangers.

26. An IGRT apparatus according to claim 25 wherein the gantry comprises one or more air directing members for directing air past the one or more heat exchangers.

27. An IGRT apparatus according to claim 26 wherein the one or more air directing members comprise one or more fans and/or one or more baffle plates.

28. An IGRT apparatus according to claim 25 wherein the gantry comprises one or more plenums for separating the one or more heat exchangers from re-circulating warmed air.

29. An IGRT apparatus according to claim 28 wherein the gantry comprises one or more plenums positioned radially inward of the one or more heat exchangers.

30. An IGRT apparatus according to claim 1 wherein the gantry comprises one or more plenums.

31. An IGRT apparatus according to claim 30 wherein each heat exchanger comprises or is positioned adjacent one or more plenums.

32. An IGRT apparatus according claim 1 wherein the gantry comprises a plurality of air-passage apertures.

33. An IGRT apparatus according to claim 1 wherein the gantry comprises an inlet for the passage of air from the gap between the gantry and the medical imaging device.

34. An IGRT apparatus according to claim 1 comprising flexible ducting for connecting the annular duct to a source of cool air.

35. An IGRT apparatus according to claim 34 further comprising a heat exchanger.

36. An IGRT apparatus according to claim 35 wherein the heat exchanger is a portable heat exchanger.

37. An IGRT apparatus according to claim 35 wherein the heat exchanger comprises an inlet for receiving warm air, one or more heat exchangers for cooling the received warm air and an outlet for expelling cooled air.

38. An IGRT apparatus according to claim 37 wherein the outlet is configured for connection to the ducting.

39. An IGRT apparatus according to claim 37 wherein the heat exchanger is connectable to a cold water system.

40. An IGRT apparatus according to claim 1 wherein the gantry comprises a static ring component and a dynamic ring component upon which a radiation source is mounted, the dynamic ring component being rotatable about the ring center.

* * * * *